US012033530B2

(12) United States Patent
Van Flute et al.

(10) Patent No.: US 12,033,530 B2
(45) Date of Patent: Jul. 9, 2024

(54) LAPAROSCOPIC SIMULATOR

(71) Applicant: Inovus Ltd, St Helens (GB)

(72) Inventors: Jordan Luke Van Flute, Widnes (GB); Elliot Roy Street, Salford Quays (GB)

(73) Assignee: INOVUS LTD, St Helens (GB)

( * ) Notice: Subject to any disclaimer, the term of this patent is extended or adjusted under 35 U.S.C. 154(b) by 0 days.

(21) Appl. No.: 17/013,797

(22) Filed: Sep. 7, 2020

(65) Prior Publication Data

US 2021/0074183 A1   Mar. 11, 2021

(30) Foreign Application Priority Data

Sep. 6, 2019 (GB) .................................. 1912903

(51) Int. Cl.
*G09B 23/30* (2006.01)
*A61B 34/10* (2016.01)
*G06F 3/01* (2006.01)

(52) U.S. Cl.
CPC .............. *G09B 23/30* (2013.01); *A61B 34/10* (2016.02); *G06F 3/011* (2013.01);
(Continued)

(58) Field of Classification Search
CPC ...... G09B 23/00; G09B 23/28; G09B 23/285; G09B 23/286; G09B 23/30; G09B 23/303;
(Continued)

(56) References Cited

U.S. PATENT DOCUMENTS 7,594,815 B2   9/2009 Toly
9,449,532 B2   9/2016 Black et al.
(Continued)

FOREIGN PATENT DOCUMENTS

WO         2016/056025 A1   4/2016
WO   WO-2018218175 A1 * 11/2018 ........... G09B 23/285

OTHER PUBLICATIONS

Porter, Michael E. and James E. Heppelmann, "How Does Augmented Reality Work?", Nov. 2017, Harvard Business Review, Magazine (Nov.-Dec. 2017) (Year: 2017).*
(Continued)

*Primary Examiner* — Kang Hu
*Assistant Examiner* — Correll T French

(57) ABSTRACT

An apparatus for laparoscopic surgical training, comprising: a physical simulator unit; a physical tissue model; and a computing and display unit; wherein the physical simulator unit comprises at least one side wall and a removable internal base plate; wherein the side wall comprises: a central opening through which a camera is arranged to view the removable internal base plate; and two or more laparoscopic surgical tools entry openings; wherein the internal base plate is arranged to hold the physical tissue model in the camera's field of view and in a position accessible to laparoscopic surgical tools when inserted in the two or more laparoscopic surgical tools entry openings; and wherein the computing and display unit is arranged to acquire video data from the camera and signal data from the physical tissue model, and to then utilise the data sets to generate and display in real-time a customised mixed reality or augmented video.

12 Claims, 11 Drawing Sheets

(52) U.S. Cl.
CPC ... *A61B 2034/102* (2016.02); *A61B 2034/105* (2016.02); *A61B 2034/107* (2016.02)

(58) Field of Classification Search
CPC ...... G09B 23/306; G09B 23/32; G09B 23/34; A61B 34/10; A61B 2034/102; A61B 2034/105; A61B 2034/107; A61B 1/313; A61B 1/3132; G06F 3/011
See application file for complete search history.

(56) References Cited

U.S. PATENT DOCUMENTS

| | | | | |
|---|---|---|---|---|
| 2006/0232664 | A1* | 10/2006 | Toly | A61B 90/30 348/45 |
| 2009/0068627 | A1* | 3/2009 | Toly | G09B 23/28 434/267 |
| 2013/0085736 | A1* | 4/2013 | Reihsen | G09B 23/28 703/11 |
| 2013/0192741 | A1* | 8/2013 | Trotta | B29C 39/123 264/294 |
| 2014/0057236 | A1* | 2/2014 | Meglan | G09B 23/30 434/274 |
| 2014/0370477 | A1 | 12/2014 | Black | |
| 2016/0140876 | A1* | 5/2016 | Jabbour | G09B 23/285 434/262 |
| 2016/0314710 | A1* | 10/2016 | Jarc | G09B 23/28 |
| 2017/0316720 | A1* | 11/2017 | Singh | A61B 90/361 |
| 2017/0352295 | A1* | 12/2017 | Belzacq | H04N 7/181 |
| 2020/0357176 | A1* | 11/2020 | Crowther | A61B 34/10 |

OTHER PUBLICATIONS

"The University of Kentucky Center for Advanced Training and Simulation Curriculum Guidelines", , Sep. 4, 2012 (Sep. 4, 2012), XP055247322, Retrieved from the Internet: URL:https://web.archive.org/web/20120904192649/http://www.mc.uky.edu/mis/MISCurriculumManual2012v1.pdf [retrieved on Feb. 4, 2016].
Extended European Search Report for EP 20194764.5 (dated Jan. 29, 2021).

* cited by examiner

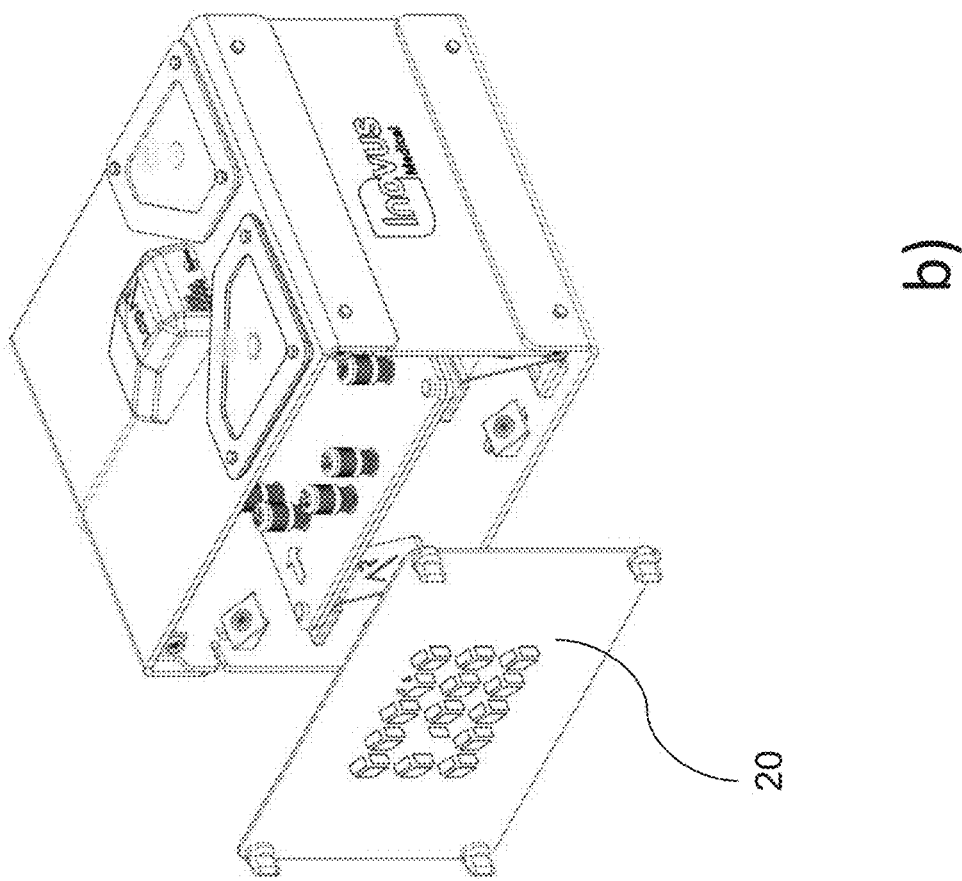
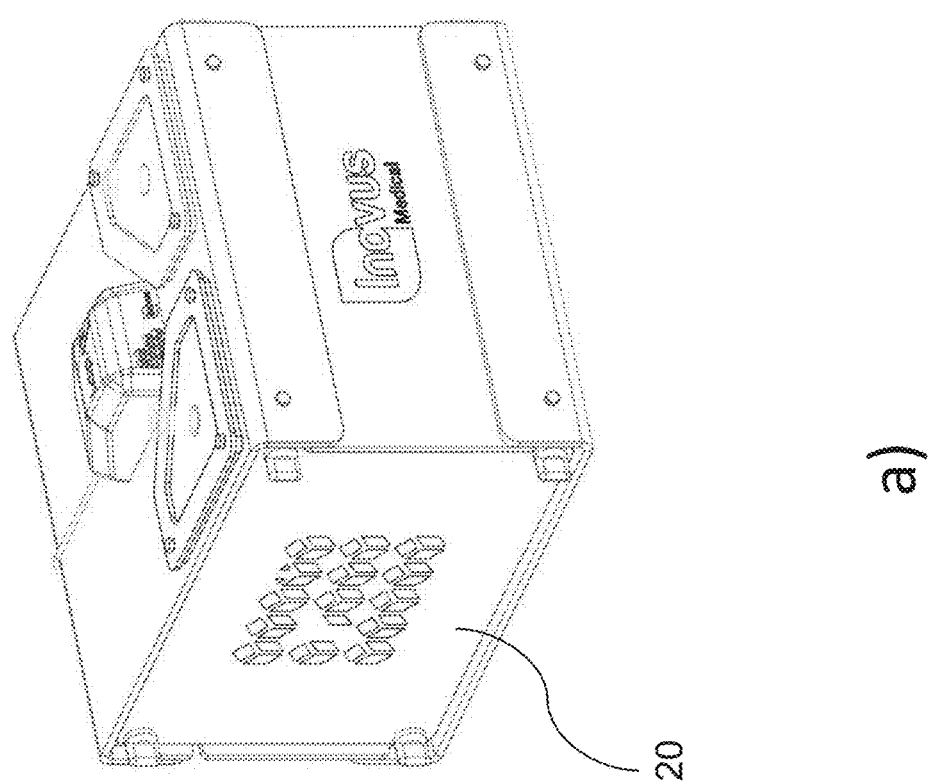
Fig. 11

LAPAROSCOPIC SIMULATOR

FIELD OF THE INVENTION

The present invention relates to an augmented and mixed reality simulator for laparoscopic surgical training. More specifically, the invention combines the physical world of performing surgery on tissue mimicking models, or phantoms, which have embedded sensors, with enhanced digital object augmentation to achieve a more realistic surgical experience. Through a process of overlaying digital textures onto real physical models, the invention allows users to engage with real tissues negating the need for artificial instrument feedback.

BACKGROUND TO THE INVENTION

Laparoscopic surgery is performed through small incisions in the abdominal wall. Procedures are carried out using elongated tools or instruments under camera view only. Minimally invasive surgeons often find it difficult to adapt to this method, struggling with both depth perception and three-dimensional perspective. This is not uncommon amongst surgeons with some taking years to achieve the desired level of ability. Certain training equipment can be used to help speed up the process, but this option is often unexplored due to the high cost involved.

Traditionally surgical training is learned by trainee surgeons through repeated practice on patients. This process can be time consuming, costly and have variable effectiveness. Consequently, the use of virtual reality and simulated practice have become an option to supplement standard training. In 2009 a study found evidence that virtual reality can improve training against standard surgical training i.e. see one do one. The trials included in the review reported decreased time to complete a task, increased accuracy, and decreased errors.

With technological advances, simulation has become a common approach to substitute clinical experiences. However, simulated educational experiences often come at great expense for training providers and clinical specialists. A 2013 report suggested that cost is often the missing outcome when evaluating simulation equipment.

The laparoscopic surgical simulation market can be split into two sections, those in the low fidelity category and those in the high fidelity. This is essentially defined by the technology that each simulator uses. Low fidelity simulators are typically described as a box trainer or more simply put a webcam in a box. This allows a surgeon to plug the simulator into a computer or monitor, insert instruments and operate under camera view as experienced in theatre. In contrast high fidelity simulators use virtual reality and haptic feedback to give the operating surgeon a more gamified experience. In most cases allowing the user to work through an entire operation from start to finish. They are in some cases also capable of generating objective metric data, enabling assessment of users over time. These simulators are often the obvious choice for training centres with much higher budgets but completely inaccessible for individual surgeons looking to train at home.

The proposed solution combines real physical medical models in a low-cost box trainer environment with overlaid digital imagery. Further development of such an affordable product should in theory see even more significant improvement in operative performance than has been previously observed in studies such as that by O'Sulivan et al 2010. This advance in technology should allow for a much-reduced upfront capital expenditure. Ultimately allowing to deliver this product to all surgeons and not just the few fortunate enough to train in centres with larger education budgets. Democratising access to surgical training around the globe.

The inventors have developed an affordable mixed reality (real and digital) laparoscopic surgical training platform simulator. The highly realistic and affordable system has the potential to democratise access to procedural based surgical simulation to be used for pre-operative surgical simulation and warm up. Allowing surgeons to access high fidelity realistic simulation for a low fidelity price point.

The invention contains all the necessary peripheral items to perform simulated laparoscopic procedures with access to the mixed reality platform and performance tracking.

The device when used as a simulation training tool provides an improved learning experience for surgical trainees that will ultimately improve performance and speed up the operative process for the benefit of the patient.

SUMMARY OF THE INVENTION

According to a first aspect of the invention there is provided an apparatus for laparoscopic surgical training, comprising:
  a physical simulator unit;
  a physical tissue model; and
  a computing and display unit;
  wherein the physical simulator unit comprises at least one side wall and a removable internal base plate;
  wherein the side wall comprises:
    a central opening through which a camera is arranged to view the removable internal base plate; and
    two or more laparoscopic surgical tools entry openings;
  wherein the internal base plate is arranged to hold the physical tissue model in the camera's field of view and in a position accessible to laparoscopic surgical tools when inserted in the two or more laparoscopic surgical tools entry openings; and
  wherein the computing and display unit is arranged to acquire video data from the camera and signal data from the physical tissue model, and to then utilise the data sets to generate and display in real-time a customised mixed reality or augmented video.

Preferably, the physical tissue model comprises tissue mimicking material embedded with internal wiring and sensors arranged to be connected to electronic circuitry, which is further connected to the computing and display unit.

Preferably, the video data acquired by the camera may be augmented in real-time and displayed in the computing and display unit to simulate the video feed of a real laparoscopic surgery.

Preferably, physical manipulation of the internal wiring and sensors in the physical tissue model by the laparoscopic surgical tools may be acquired as signal data, which signal data may then be used to generate in real-time a customised video augmentation to the video feed acquired by the camera, and a merged video is displayed in the computing and display unit.

Preferably, manipulation of the physical tissue model with the laparoscopic surgical tools may be augmented in real-time and displayed in the computing and display unit.

Preferably, the angle on the camera's principal axis may be arranged to be perpendicular to the plane of the internal base plate.

Preferably, the angle on the camera's principal axis may be substantially at 30 degrees to the plane of the side wall.

Preferably, the internal base plate is at an incline, which imaginary continuation plane may be substantially at 30 degrees with the side wall.

Preferably, the internal base plate may comprise a pigmented silicone background, which background is then used in the augmented video to project multiple backgrounds onto the surface during different procedures that occur in several regions of the body.

Preferably, the physical tissue model may be replaceable and reconnectable to the circuitry, and wherein the physical tissue model is arranged to represent various human or animal tissue shapes, sizes and consistency, and the computing and display unit is programmable to represent an augmented video compatible with said tissue.

Preferably, the camera may be arranged to track and extract data of the displacement of the physical tissue model, which data is then used to generate visual representations of said tissue in the augmented video.

Preferably, the camera may be arranged to track and extract data of three dimensional movements of the customised laparoscopic surgical tools inserted in the surgical tools entry openings, which data is then used to generate visual representations of the laparoscopic tools in the augmented video.

Preferably, two or more cameras may be arranged to acquire stereoscopic or other forms of depth related information from their field of view.

Preferably, the camera may be in a camera housing, which housing further comprises lighting arranged to illuminate the inside of the physical simulator unit, wherein the lighting is in the visible spectrum, infrared, a combination of the above, or a combination of colours arranged to enhance or discard for the camera elements of the physical tissue model, the background or of the laparoscopic tools.

Preferably, the physical simulator unit may be in the shape of a box and comprises a top panel, a bottom panel, two parallel fixed side panels, two further side panels which are removable and parallel to each other; and wherein the side wall is the top panel.

BRIEF DESCRIPTION OF THE DRAWINGS

The invention will now be described by way of example only with reference to the accompanying drawings in which:

FIG. 11 are illustrations of the physical simulator unit, showing a removable side panel, in an closed position in a) and in a open position in b), wherein the replaceable physical tissue model is inserted.

DETAILED DESCRIPTION OF THE INVENTION

The present invention relates to an augmented and mixed reality simulator for laparoscopic surgical training. More specifically, the invention combines the physical world of performing surgery on tissue mimicking models, or phantoms, which have embedded sensors, with enhanced digital object augmentation to achieve a more realistic surgical experience. Through a process of overlaying digital textures onto real physical models, the invention allows users to engage with real tissues negating the need for artificial instrument feedback. The digital textures can also be used to create complications such as bleeding, perforations and more on otherwise inanimate objects.

Figure 1:
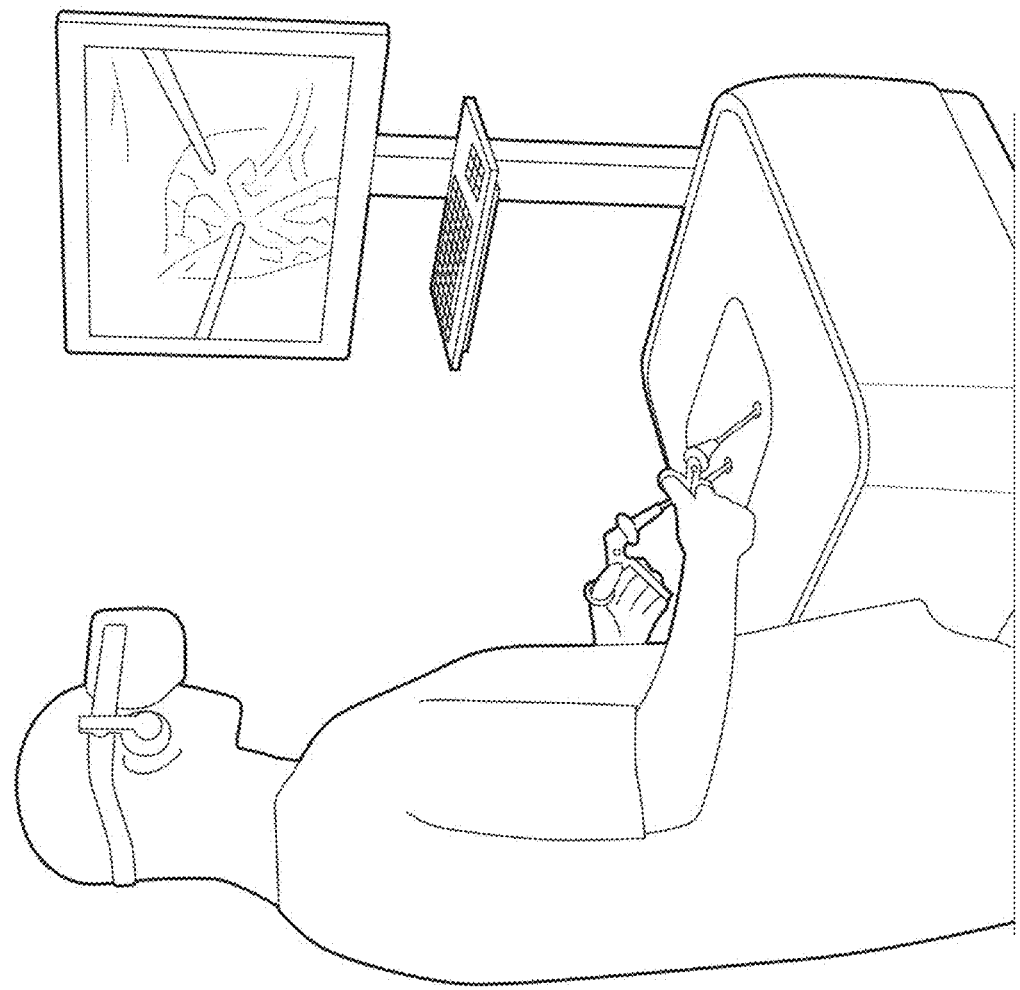
FIG. 1 shows a high fidelity, high cost simulator with Virtual Reality that allows highly simulated surgical procedure simulations.

FIG. 1 shows a high fidelity, high cost simulator, such as e.g. the Lap Mentor from Simbionix. This is a VR system that allows full surgical procedures to be performed with performance metric output generated for each user. These simulators are often criticised for their lack of real to life tactile feedback felt through the instruments due to the nature of motor driven haptics.

Figure 2:
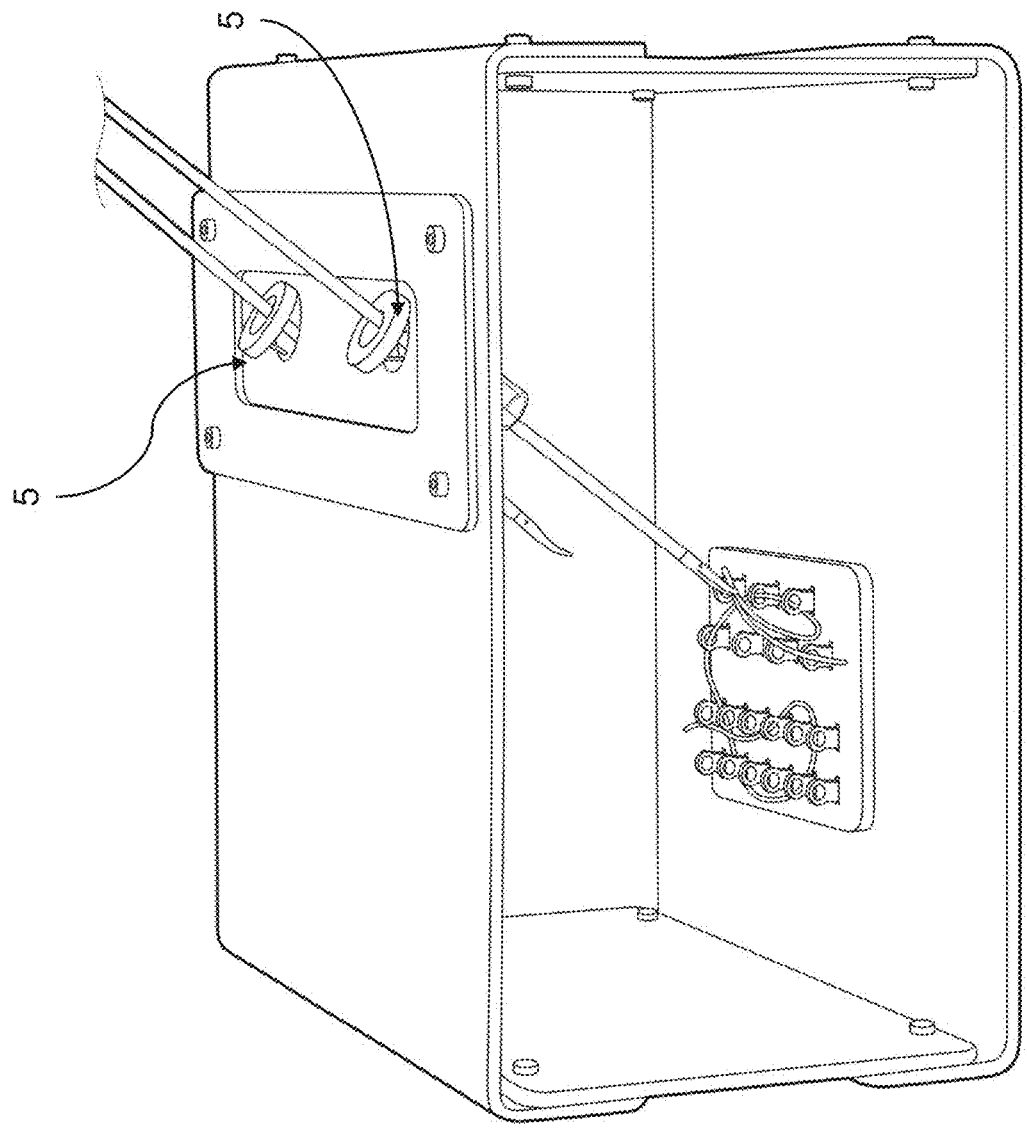
FIG. 2 shows a low fidelity, low cost laparoscopic box trainer.

FIG. 2 shows a low cost, low fidelity laparoscopic box trainer into which the user can place a variety of tasks and operate on them with real laparoscopic instruments, in this case the image is streamed onto your laptop giving the training surgeon a really good understanding of issues like the fulcrum effect, triangulation and depth perception. These simulators are often criticised for their lack of realism and objective feedback.

Figure 3:
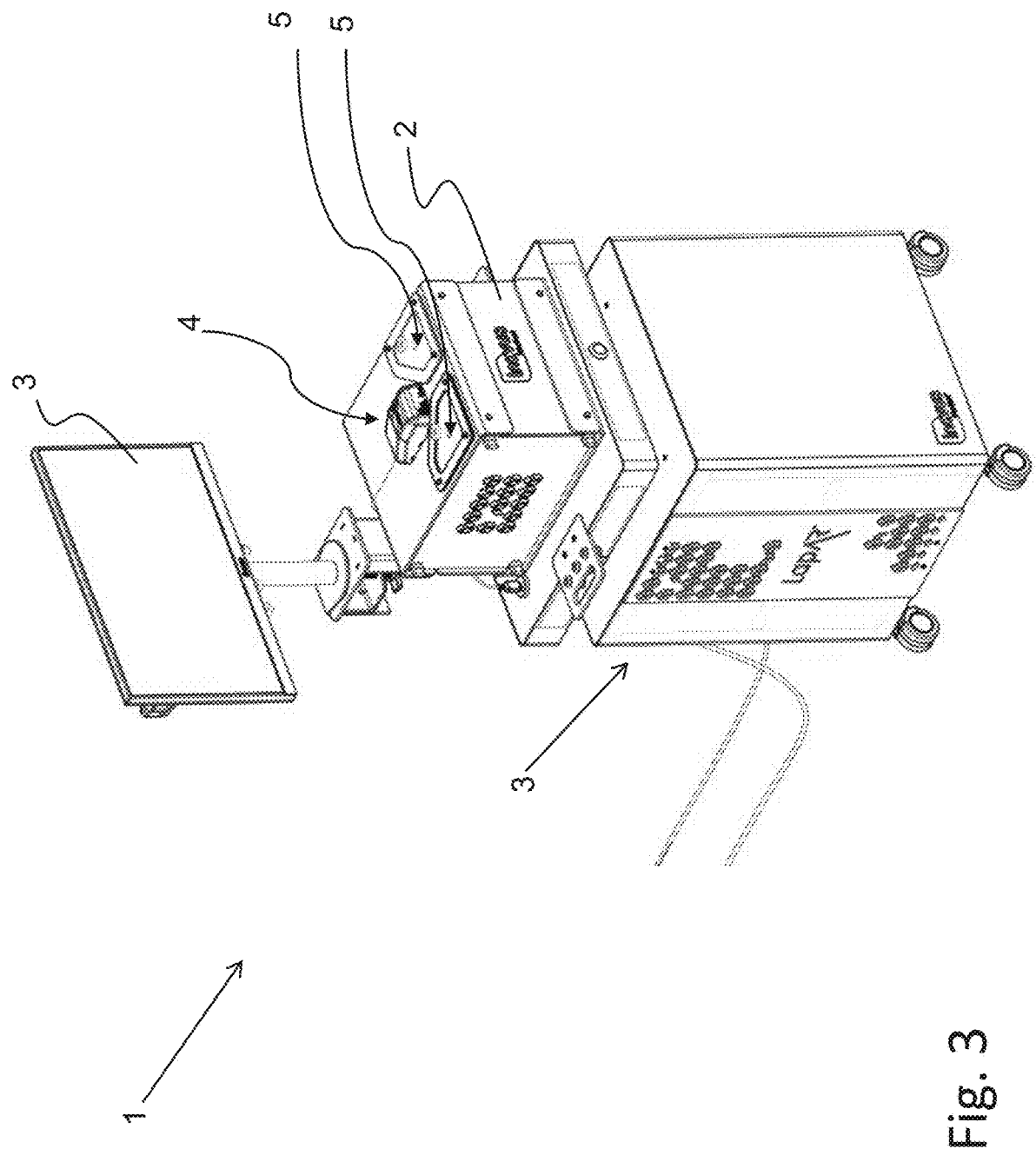
FIG. 3 shows an illustration of high fidelity, low cost simulator in accordance with of the invention, showing a physical simulator unit with surgical tools entry openings and a display arranged to show live augmented visual representations of the procedure.
Figure 4:
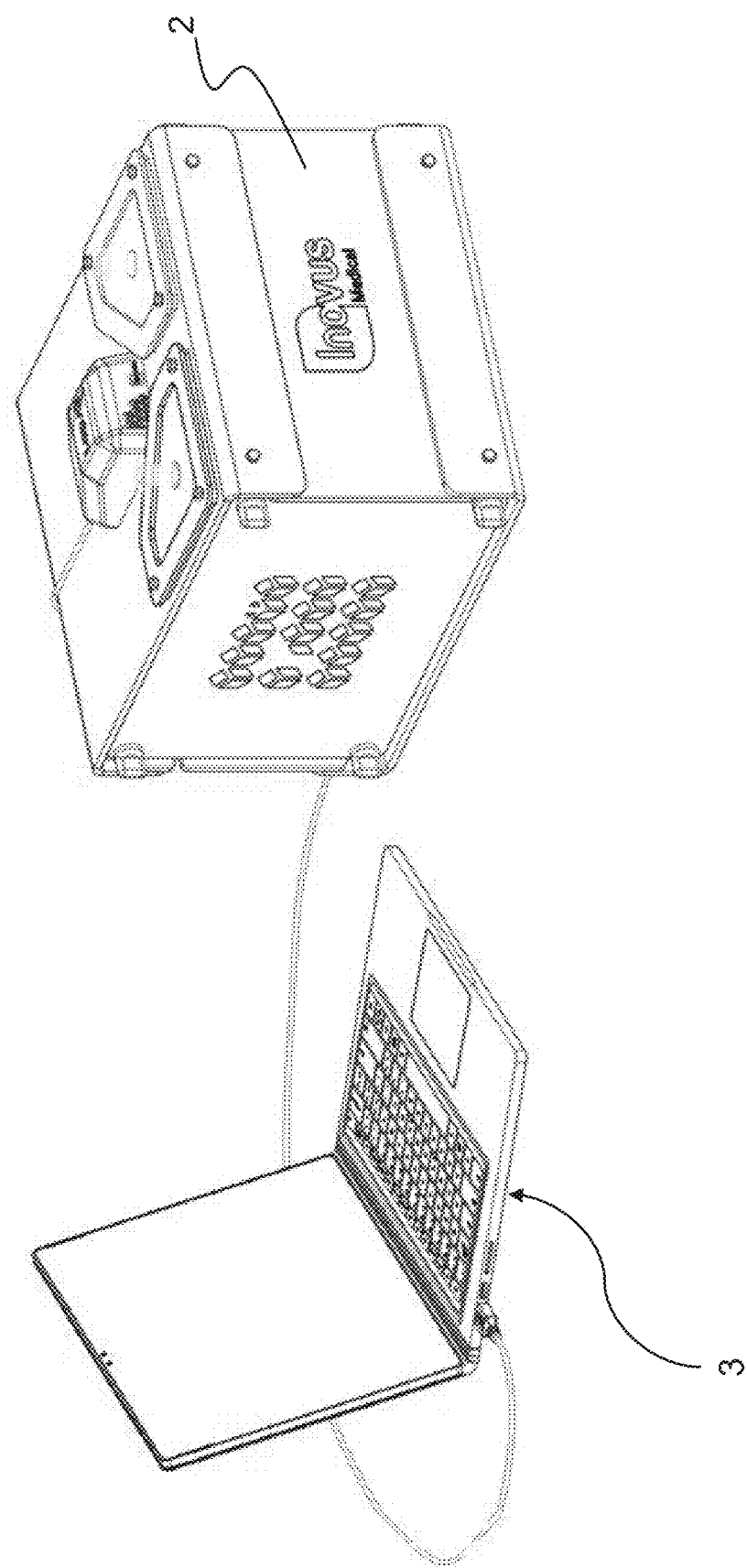
FIG. 4 shows a portable embodiment of high fidelity, low cost simulator in accordance with the invention, showing a physical simulator unit with surgical tools entry openings and a laptop arranged to show live augmented visual representations of the procedure.

FIGS. 3 and 4 show the proposed invention. The invention merges real feel tissue models with a digital environment to provide real to life haptics, an immersive environment and full procedure training on a simple, accessible and affordable laparoscopic procedure trainer.

More specifically FIG. 3 shows a laparoscopic surgical training device 1 comprising a physical simulator unit, also referred to a box trainer 2, and a computing and display unit 3.

FIG. 4 shows a more portable embodiment to the invention in FIG. 3.

Figure 5:
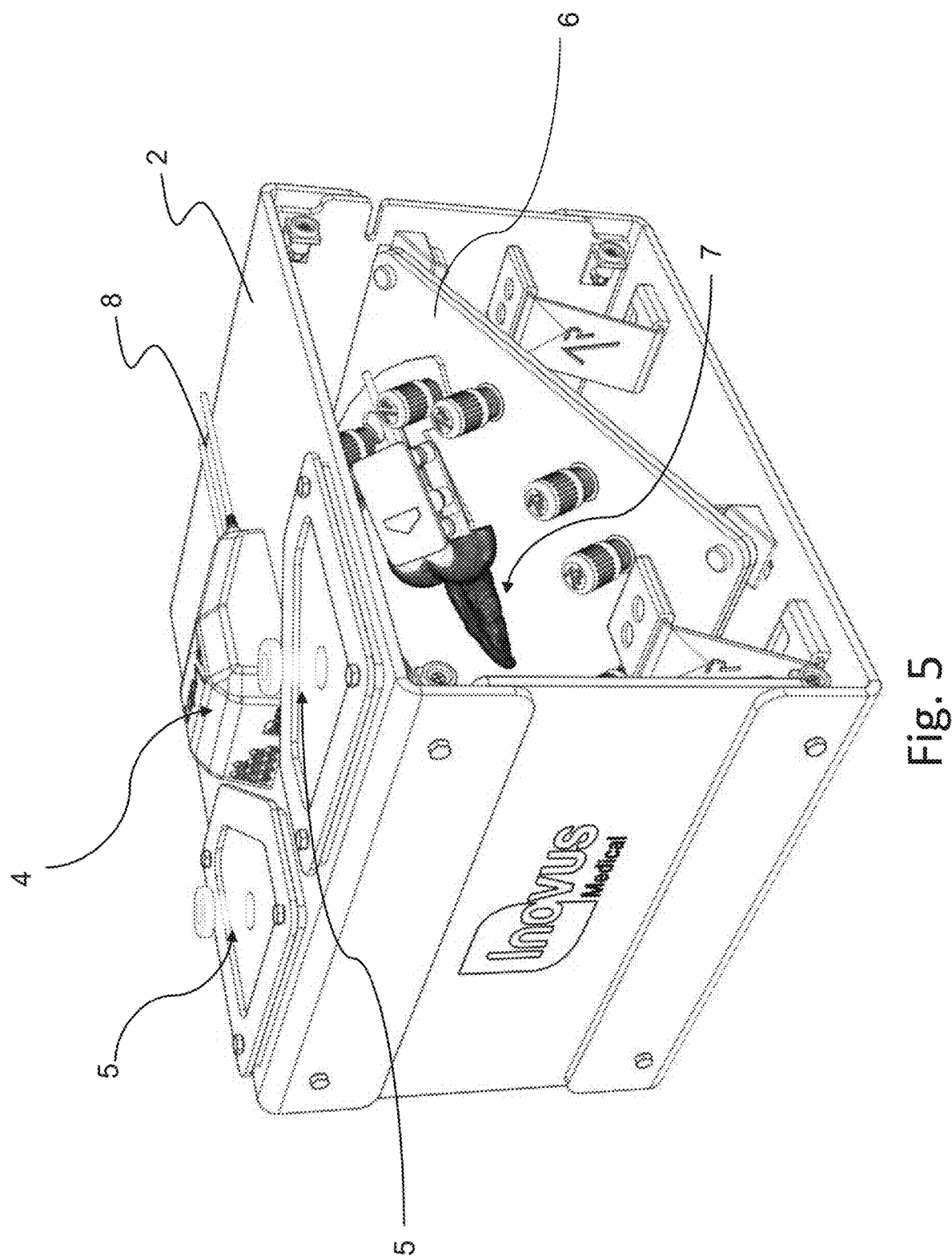
FIG. 5 shows a clearer illustration of the physical simulator unit, with a side panel removed, allowing the viewing of a physical tissue model inside the unit, further showing surgical tools entry openings and a camera housing, in accordance with of the invention.

Referring now to FIG. 5, a closeup perspective view of the physical simulator unit 2 is shown. The physical simulator unit 2 is in the shape of a box and comprises a top panel, a bottom panel, two parallel fixed side panels and two further parallel side panels which are removable.

A camera housing 4 is installed on the top panel. The camera housing comprises a camera (not visible in the Figures). A central opening in the top panel allows the camera to see inside the physical simulator unit. The camera housing 4 may further comprise lighting arranged to illuminate the inside of the box trainer 2. The lighting may be at full visible spectrum, Infrared, or a combination of the above.

In this embodiment the camera's line of sight is arranged to be substantially at a 30-degree angle with the plane of the top panel. The camera, camera box, the lighting and any other optical sensors in the camera housing 4 are connected to the computing and display unit 3 via electronic and computing cabling 8.

It will be appreciated that the computing and display unit 3 may be any known computing device such as desktops, laptops, tablets or custom units that are capable of acquiring, processing and displaying video and image data, as well as capable of controlling electronics such as lighting, power and sleep modes.

Referring again to FIG. 5, two laparoscopic surgical tools entry openings 5 are shown close to adjacent corners of the top panel.

During the training procedure the laparoscopic surgical tools are inserted in the tool entry openings 5 in a similar manner as shown in FIG. 2.

As with all laparoscopic or image guided procedures the simulator occludes the surgeons view of the physical models inside, requiring them to perform each task via a monitor or screen. Instruments are inserted via the entry ports located on the top of the simulator.

The physical simulator unit 2 further comprises a removable internal base plate 6. A removable physical tissue model 7 is installable on the removable internal base plate. The camera is arranged to view the removable internal base plate through the central opening.

The camera may be a wired camera, such as USB, or an image data acquisition and it is orientated at a 30-degree angle and is perpendicular to the removable magnetic base inside of the simulator. The camera observes the image as it is in reality, then using a combination of marker based augmented reality and background compositing the image that the user sees on the monitor is transformed into a mixed reality experience.

The position and angle of the physical tissue model 7 is adjustable. Likewise the position and angle of internal base plate 6 is also adjustable.

Figure 6:
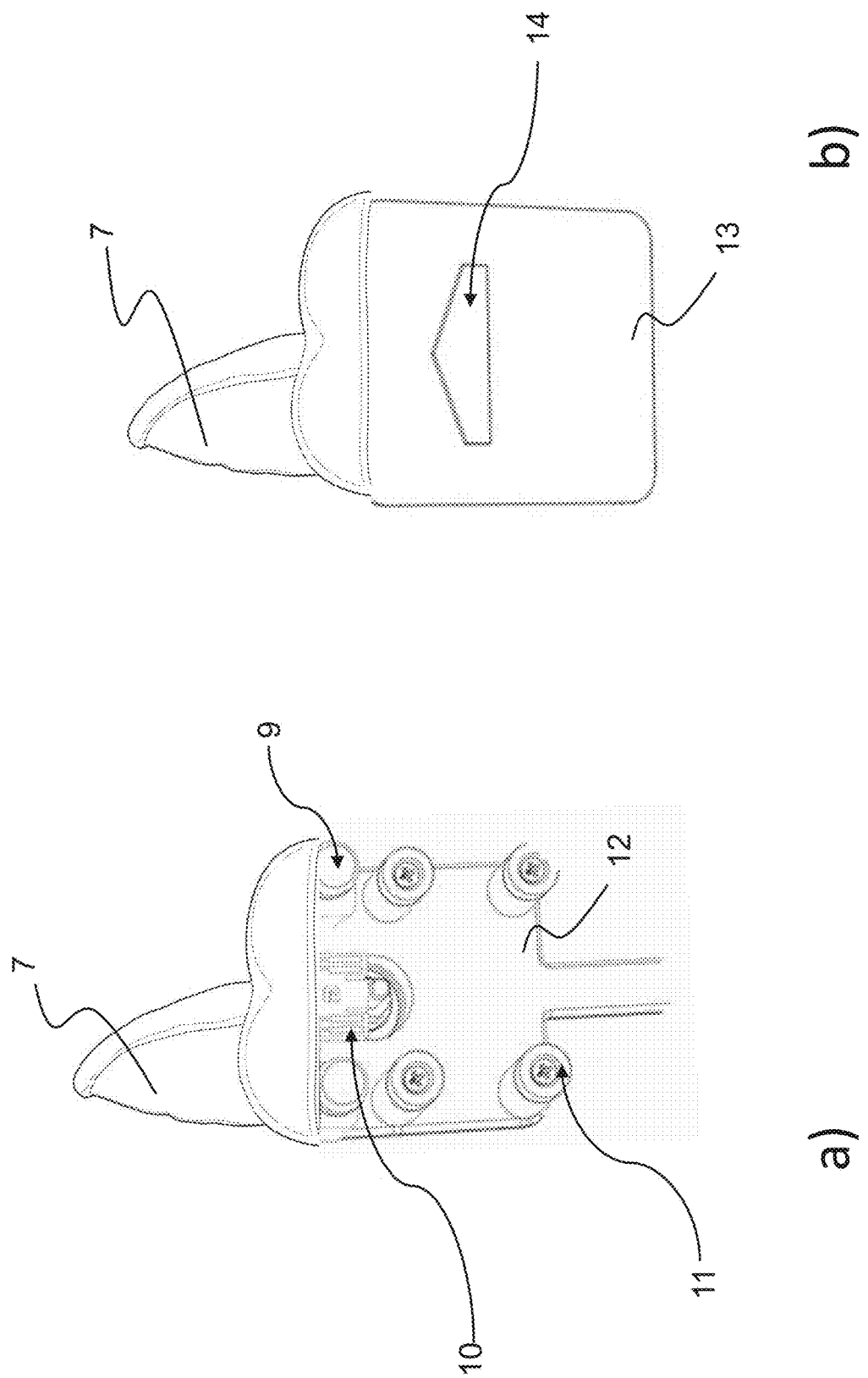
FIG. 6A shows the replaceable physical tissue model and its electronic and mechanical connections.
FIG. 6B shows the tissue model with a cover with an image acquisition trace.

FIG. 6A shows an illustration of a removable physical tissue model 7. The physical tissue model 7 is made of realistic silicone or synthetic tissue models designed to mimic the feel of real anatomical structures. One or more retainers 9 made of stretchy silicon and part of the physical tissue model 7 connect and retain the model onto a model base 12. Screws 11 fasten the model base 12 onto the internal base plate 6.

The tissue model 7 may be of latex or silicon or other materials or plastics, which are constructed in different layers to mimic the resilience of different types of anatomical tissues.

The inventions use of realistic silicone or synthetic tissue models designed in some cases to work with electro surgical instruments to mimic the feel of real anatomical structures, takes simulated practice to the next level, by allowing surgeons to practice with the same instruments used regularly in theatre.

The physical tissue model 7 may be embedded with wiring and or electronic sensors. Electrical connectors 10 connect the tissue model 7 to electric circuitry and then to the computing and display unit 3.

FIG. 6B shows a model cover 13 which mates with model base 12 and covers the screws and connectors. An image acquisition trace 14 is sketched, embossed or printed on the model cover 13. In this embodiment the trace is a stretched pentagon. The trace is acquired by the camera. Other shapes may be used to identify to the computing unit 3 the tissue model type. The model cover 13 may comprise other identifiable information, e.g. barcodes, alphanumeric etc. e.g. to be read by the camera and to tag a surgical students name and surgical simulation performance.

Whilst computer vision could be entirely relied upon across all system features, embedded sensors in the physical tissue model 7 act as a more reliable and robust trigger for complications that occur during interaction with the physical models inside of the simulator.

Figure 7:
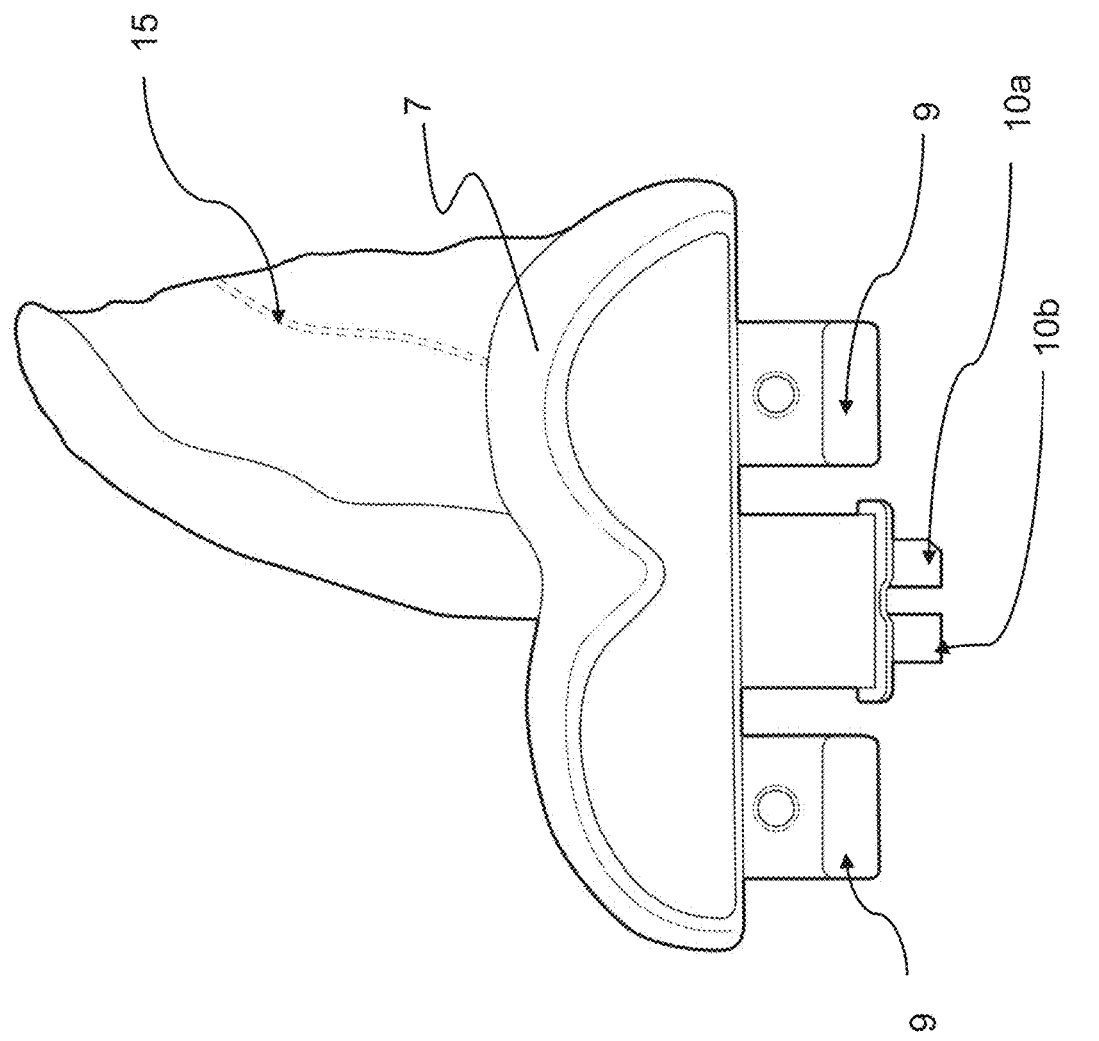
FIG. 7 shows the physical tissue model highlighting the track of an embedded sensor, in accordance with an embodiment of the invention.

FIG. 7 shows another embodiment of a physical tissue model 7, showing electrical connectors 10a and 10b and retainers 9. FIG. 7 further shows a wiring 15 embedded in the body of the tissue model 7.

In this embodiment copper magnet wire is used. However it will be appreciated that various conductive wires with various conductive properties may be used to simulate and be programmed and tissue response simulators.

In this embodiment, one end of the wiring 15 is connected to electrical connectors 10a and the other end of the wiring is connected to electrical connectors 10b, thus electrically looping the two connectors 10a 10b.

The wiring 15 may be embedded in different shapes and loops inside the tissue model 7 to represent e.g. a blood vessel or other ligament. In this embodiment the wiring 15 is twisted to form one elongated blood vessel track.

Figure 8:
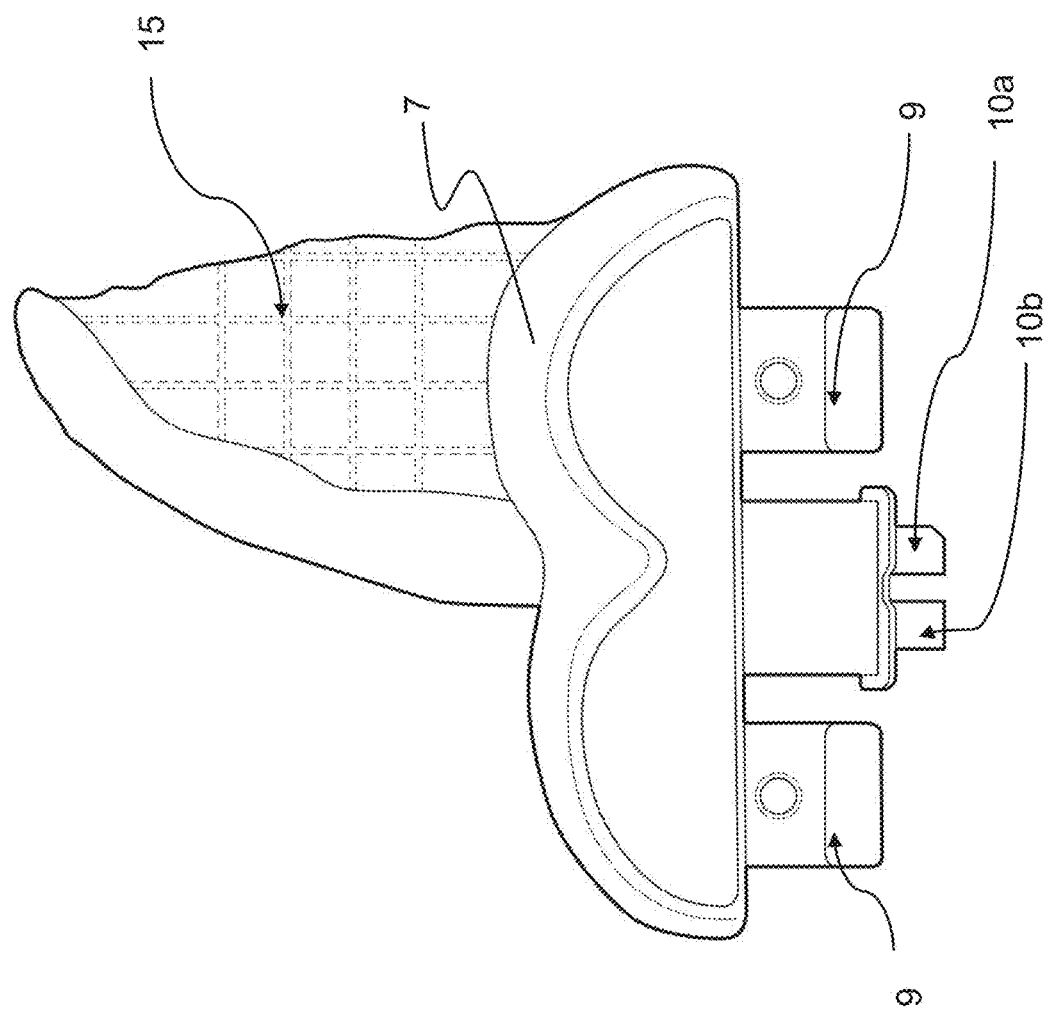
FIG. 8 shows the physical tissue model highlighting the track of a more complex embedded sensor or sensors, in accordance with a second embodiment of the invention.

FIG. 8 shows another embodiment of the wiring 15, which may be a two-dimensional mesh and identify the 2D location of the cut.

The mouldable material of the tissue model 7 may be doped e.g. with metal or carbon particles that change the impedance and or magnetic properties of the structure and of the tissue model, or phantom.

The tissue model 7 may also employ force sensitive resistors, accelerometers or tensions sensors.

Figure 9:
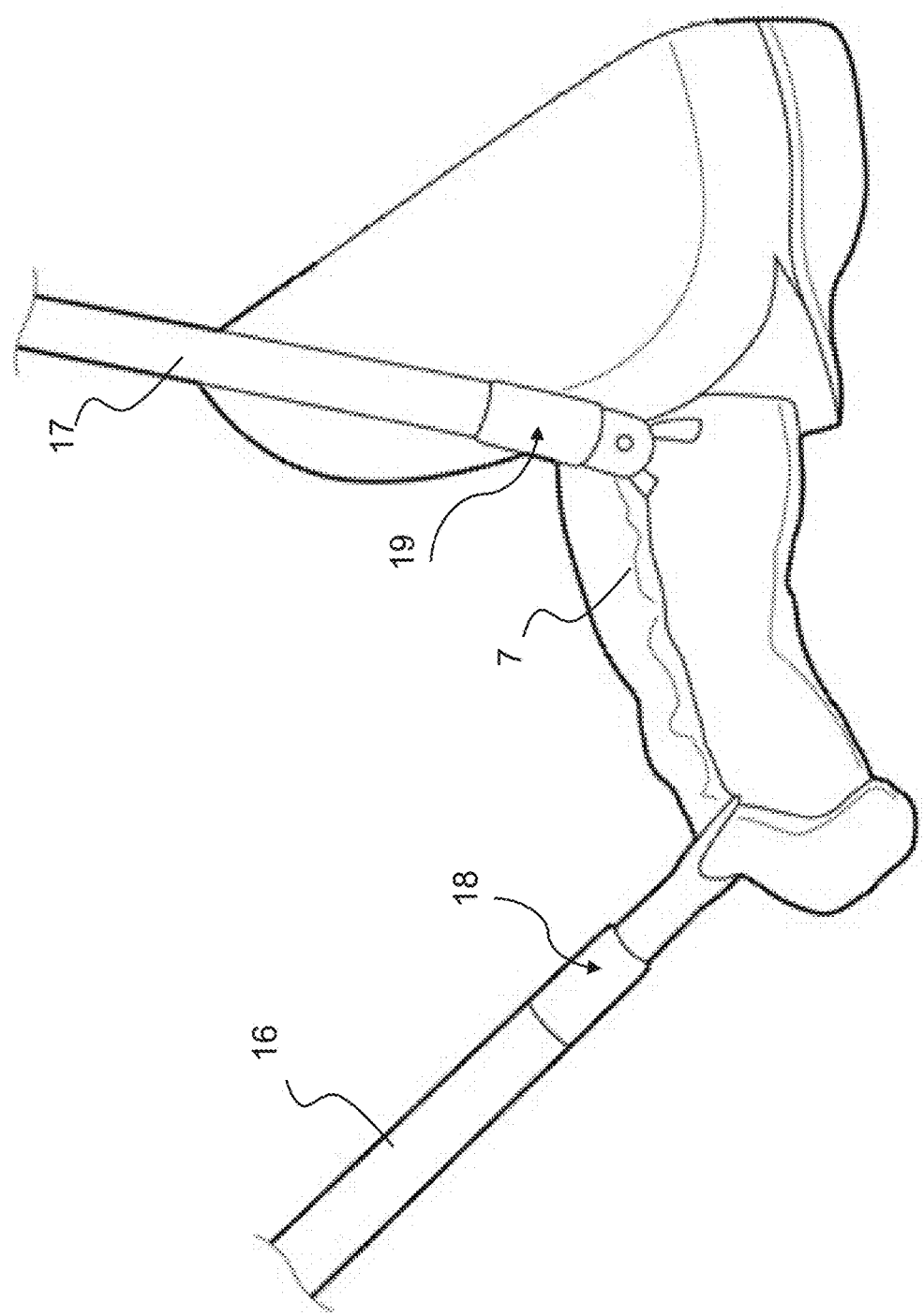
FIG. 9 shows a close-up illustration of simulated surgery being performed on the physical tissue model, further showing trace marks of the laparoscopic tools.

Referring now to FIG. 9, during a laparoscopy simulation, using laparoscopic gripper 16 and scissor 17, when cutting through the tissue model, the wiring 15 may become cut and thus create an open circuit which will be identified by the signal data acquisition and the computing and display unit. An augmented representation of the bleeding may then be shown on the display unit, in the area of the cut. Thus simulating a real-life surgical event.

When cut with a laparoscopic instrument the magnet wire connection is lost and the bleed is triggered through a change in system state that communicates with the AR software. The rig markers mentioned above determine the bleeding point in the digital environment. This solution can be used across a myriad of procedures and can be used to trigger different intraoperative complications (bleeding, bowel perforation, perforated common biliary tree). As such, individual solutions for triggering complications will not be required and this approach can be used to standardise this aspect of the simulator across all procedures.

The combined reliance on both computer vision and physical sensors results in a more stable system, devoid of the usual bugs found in programs reliant solely on one or the other.

In addition to solving issues with tactile feedback and realism, the system is also capable of generating accurate objective performance feedback using real laparoscopic tools.

Figure 10:
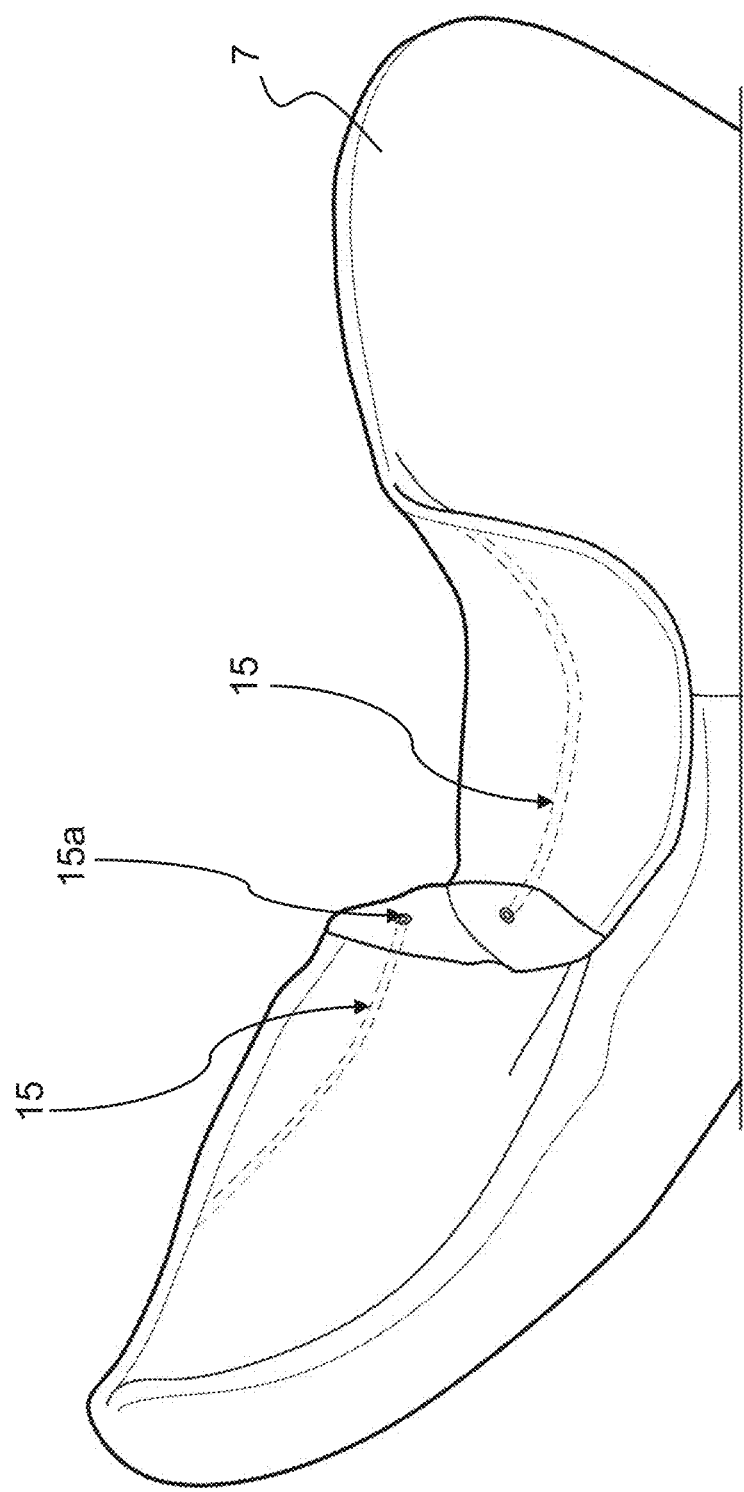
FIG. 10 shows the surgery result on the physical tissue model highlighting the cut track of an embedded sensor.

FIG. 10 illustrates a tissue model 7 with a cut internal wiring 15, showing the wiring cut location 15a.

In more detail, in the case of the first release, the vascular sensor is connected to the bridge during the entire operation. This sensor is formed of a sheathed copper magnet wire, designed for low voltage applications. The software platform performs a search for a connection upon start-up, once confirmed the procedure can be carried out. If the vascular sensor detects an incision, the information is instantly fed back to the software so that the relevant complication occurs e.g. bleeding. The user is then prompted to rectify the bleed and is guided through the necessary steps to resolve the complication. More advanced users may decide to use a surgical knots/loops to tie off the vessel before making an incision. In this case, the user can confirm that a series of loops have been placed correctly thus turning off the bleed trigger during the remainder of the procedure.

Referring again to FIG. 9, gripper tracer 18 and scissor tracer 19 are visible to the camera, which read and via the computing unit 3 calculates the three-dimensional position of the laparoscopic tools, which is then generated and displayed as an augmented images on the display.

Referring to FIG. 11 the physical simulator unit is shown with a removable side panel 20 in a closed position in a) and in an open position in b). The inner panel 6 and replaceable physical tissue model 7 are inserted form the opening created from the side panel 20.

Therefore, the invention describes an apparatus for laparoscopic surgical training, which comprises a physical simulator unit; a physical tissue model; and a computing and display unit; wherein the physical simulator unit comprises at least one side wall and a removable internal base plate; wherein the side wall comprises: a central opening through which a camera is arranged to view the removable internal base plate; and two or more laparoscopic surgical tools entry openings; wherein the internal base plate is arranged to hold the physical tissue model in the camera's field of view and in a position accessible to laparoscopic surgical tools when inserted in the two or more laparoscopic surgical tools entry openings; and wherein the computing and display unit is arranged to acquire video data from the camera and signal data from the physical tissue model, and to then utilise the data sets to generate and display in real-time a customised mixed reality or augmented video.

The physical tissue model comprises tissue mimicking material embedded with internal wiring and sensors arranged to be connected to electronic circuitry, which is further connected to the computing and display unit.

The video data acquired by the camera is augmented in real-time and displayed in the computing and display unit to simulate the video feed of a real laparoscopic surgery.

The physical manipulation of the internal wiring and sensors in the physical tissue model by the laparoscopic surgical tools is acquired as signal data, which signal data is then used to generate in real-time a customised video augmentation to the video feed acquired by the camera, and a merged video is displayed in the computing and display unit.

The manipulation of the physical tissue model with the laparoscopic surgical tools is augmented in real-time and displayed in the computing and display unit.

The angle on the camera's principal axis is arranged to be perpendicular to the plane of the internal base plate.

The angle on the camera's principal axis is substantially at 30 degrees to the plane of the side wall.

The internal base plate is at an incline, which imaginary continuation plane is substantially at 30 degrees with the side wall, also known as top panel. The device has an angled platform, allowing the camera view to be perpendicular to the plane of the operative field. This is extremely important to ensure the instrument tracking aspect of the software is accurate. The camera position has been altered for optimal functionality of the software. Some optional side skirts have been added to help standardise the light conditions within the system and optimise the performance of the software.

The simulators design plays an integral part in the users mixed reality experience, ensuring that quality and realism remains uninterrupted throughout the procedure. Side panels and plastic surface texture are among some of the modifications required to prevent light disturbance inside of the simulator. These changes also optimise the simulators ability to track instruments in real time during a procedure.

A proprietary pigment blend has been used as to form the silicone background in the simulator for purpose of stable compositing of the surface. This is used to project multiple backgrounds onto the surface during different procedures that occur in several regions of the body. The colour was developed for specific use inside of the simulator so as not occlude instruments or tools.

The internal base plate may comprise a pigmented silicone background, which background is then used in the augmented video to project multiple backgrounds onto the surface during different procedures that occur in several regions of the body.

The physical tissue model may be replaceable and reconnectable to the circuitry, and wherein the physical tissue model is arranged to represent various human or animal tissue shapes, sizes and consistency, and the computing and display unit is programmable to represent an augmented video compatible with said tissue.

The camera may be arranged to track and extract data of the displacement of the physical tissue model, which data is then used to generate visual representations of said tissue in the augmented video.

The camera may be arranged to track and extract data of three dimensional movements of the customised laparoscopic surgical tools inserted in the surgical tools entry openings, which data is then used to generate visual representations of the laparoscopic tools in the augmented video.

Two or more cameras may be arranged to acquire stereoscopic or other forms of depth related information from their field of view.

The camera may be in a camera housing, which housing further comprises lighting arranged to illuminate the inside of the physical simulator unit, wherein the lighting is in the visible spectrum, infrared, a combination of the above, or a combination of colours arranged to enhance or discard for the camera elements of the physical tissue model, the background or of the laparoscopic tools.

The physical simulator unit may be in the shape of a box and comprises a top panel, a bottom panel, two parallel fixed side panels, two further side panels which are removable and parallel to each other; and wherein the side wall is the top panel.

The following table compares the features of the low and high-fidelity simulators vs the simulator proposed by the invention.

|  | Low Fidelity | High Fidelity | Inovus LAP AR |
| --- | --- | --- | --- |
| Accessible | YES | NO | YES |
| Affordable | YES | NO | YES |
| Full Procedure Simulation | NO | YES | YES |
| Performance Tracking | NO | YES | YES |
| Validated Curriculum | NO | NO | YES |
| Realistic Haptics | YES | NO | YES |
| Immersive and engaging | NO | YES | YES |

The invention employs computer vision to deliver a stable dynamic environment in which to operate. The invention uses a unique approach to marker-less three-dimensional instrument tracking. This allows the creation of extremely accurate movement metrics for users and provides a platform to assess performance over time in a plethora of procedures. Reducing the barrier to entry on such products will allow for much larger data collection than previously possible using high fidelity systems. This is made possible through the utilisation of several computer vision-based techniques, including but not limited to Canny edge detection and Hough line tracking. A proprietary software algorithm is used to generate performance data.

The inventions marker-less tracking enables on screen interaction with virtual action buttons. This allows the operating surgeon to carry out 'in play' actions and work through steps of the procedure without having to down tools.

The core features of the simulator include:

Close to life haptic feedback through synthetic soft tissue models

Realistic digital anatomy fully integrated with the soft tissue models

Ability to create and manage intraoperative complications

Marker-less 3D movement tracking of the instruments within the surgical field with objective feedback on the key metrics of surgical performance achieved through monocular camera lens Online user accounts allow users to store and track progress of their surgical training Online training portals allow trainees to perform and record surgical procedures specific to their specialty Full procedure simulation across general (including paediatric) surgery, O&G and Urology Performance tracking and feedback compatible with generic skills tasks and validated curricula such as the LapPass programme.

The invention achieves consistent image registration of the digital anatomy.

The invention can be adapted to provide augmented reality procedures for general, paediatric, O&G and Urological surgery including but not limited to: Cholecystectomy, Bowel anastomosis, Pyloromyotomy, Ectopic pregnancy, Myomectomy, Vaginal Vault closure and Nephrectomy.

The IP is obfuscated within codebase and cannot be accessed without access to protected source files garnering the necessary level of protection once the product is commercialised.

The technical solution proposed by the application is a major advance on the current state of the art. When considering performance tracking of laparoscopic simulation, the existing box trainer products are designed to track performance related to basic 'generic tasks' only. None of the existing technology has the ability to track performance related to 'procedure specific' full surgical tasks.

The only way to track performance in full surgical procedures is with extremely expensive VR simulators, thus making the proposed invention unique in form and function.

The invention claimed is:

1. An apparatus for laparoscopic surgical training, comprising:

a physical simulator unit;

a physical tissue model; and a computing and display unit;

wherein the physical simulator unit comprises at least one side wall and a removable internal base plate;

wherein the side wall comprises:

a central opening through which a camera is arranged to view the removable internal base plate; and two or more laparoscopic surgical tools entry openings;

wherein the internal base plate is arranged to hold the physical tissue model in the camera's field of view and in a position accessible to laparoscopic surgical tools when inserted in the two or more laparoscopic surgical tools entry openings; and wherein the computing and display unit is arranged to acquire video data from the camera and signal data from the physical tissue model, and to then utilize the data sets to generate and display in real-time a customized mixed reality or augmented video;

wherein the video data acquired by the camera is augmented in real-time and displayed in the computing and display unit to simulate the video feed of a real laparoscopic surgery;

wherein the physical tissue model comprises tissue mimicking material embedded with internal wiring and sensors arranged to be connected to electronic circuitry, which is further connected to the computing and display unit;

wherein an electrical connection check between the internal wiring and the electronic circuitry is performed upon start-up of the apparatus;

wherein when cutting through the physical tissue model, with the laparoscopic surgical tools by a user, and the internal wiring is cut, an open circuit is identified by the signal data acquisition and the computing and display unit, which then triggers and generates an augmented representation of bleeding in the area of the cut, thus augmenting the video feed acquired by the camera, and a merged video is displayed in the computing and display unit, thus simulating a real-life surgical event;

wherein the cutting of the physical tissue model with the laparoscopic surgical tools is augmented in real-time and displayed in the computing and display unit via overlaying digital textures on the physical tissue model and via acquiring, processing and displaying the video data and the signal data; and wherein the open circuit of the internal wiring prompts the user to rectify the bleed by using the laparoscopic surgical tools to tie off the cut wiring, reestablishing an electrical connection with the electronic circuitry and thus turning off the bleeding trigger.

2. The apparatus of claim 1, wherein the angle on the camera's principal axis is arranged to be perpendicular to the plane of the internal base plate.

3. The apparatus of claim 2, wherein the angle on the camera's principal axis is substantially at 30 degrees to the plane of the side wall.

4. The apparatus of claim 1, wherein the internal base plate is at an incline, which imaginary continuation plane is substantially at 30 degrees to the plane of the side wall.

5. The apparatus of claim 1, wherein the internal base plate comprises a pigmented silicone background, which background is then used in the augmented video to project multiple backgrounds onto the surface during different procedures that occur in several regions of the body.

6. The apparatus of claim 1, wherein the physical tissue model is replaceable and reconnectable to the circuitry, and wherein the physical tissue model is arranged to represent various human or animal tissue shapes, sizes and consistency, and the computing and display unit is programmable to represent an augmented video compatible with said tissue.

7. The apparatus of claim 1, wherein the camera is arranged to track and extract data of the displacement of the physical tissue model, which data is then used to generate visual representations of said tissue in the augmented video.

8. The apparatus of claim 1, wherein the camera is arranged to track and extract data of three dimensional movements of the laparoscopic surgical tools inserted in the surgical tools entry openings, which data is then used to generate visual representations of the laparoscopic surgical tools in the augmented video.

9. The apparatus of claim 1, wherein two or more cameras are arranged to acquire stereoscopic depth related information from their field of view.

10. The apparatus of claim 1, wherein the camera is in a camera housing, which housing further comprises lighting arranged to illuminate the inside of the physical simulator unit, wherein the lighting is arranged to enhance or discard for the camera elements of the physical tissue model, the background or of the laparoscopic tools.

11. The apparatus of claim 1, wherein the physical simulator unit is in the shape of a box and comprises a top panel, a bottom panel, two parallel fixed side panels, two further side panels which are removable and parallel to each other; and wherein the side wall is the top panel.

12. A method for laparoscopic surgical training, comprising the steps of:
holding a physical tissue model in a camera's field of view and in a position accessible to laparoscopic surgical tools;
acquiring video data from the camera and signal data from the physical tissue model;
generating and displaying in real-time a customized mixed reality or augmented video from the video and the signal data;
wherein the physical tissue model comprises tissue mimicking material embedded with internal wiring and sensors arranged to be connected to electronic circuitry, which is further connected to a computing and display unit;
augmenting the video data acquired by the camera in real-time and displaying in the computing and display unit to simulate the video feed of a real laparoscopic surgery;
wherein an electrical connection check between the internal wiring and the electronic circuitry is performed upon start-up of the apparatus;
wherein when cutting through the physical tissue model, with the laparoscopic surgical tools by a user, and the internal wiring is cut, an open circuit is identified by the signal data acquisition and the computing and display unit, which then triggers and generates an augmented representation of bleeding in the area of the cut, thus generating in real-time a customized video augmentation to the video feed acquired by the camera; and
merging and displaying the video augmentation and the video feed in the computing and display unit, thus simulating a real-life surgical event;
wherein the cutting the physical tissue model with the laparoscopic surgical tools is augmented in real-time and displayed in the computing and display unit via overlaying digital textures on the physical tissue model and via acquiring, processing and displaying the video data and the signal data; and
wherein the open circuit of the internal wiring prompts the user to rectify the bleed by using the laparoscopic surgical tools to tie off the cut wiring, reestablishing an electrical connection with the electronic circuitry and thus turning off the bleeding trigger.

* * * * *